(12) United States Patent
Juarez

(10) Patent No.: US 9,125,956 B2
(45) Date of Patent: Sep. 8, 2015

(54) ELECTRICAL LIGHTING AND HEATING MODULES, ASSEMBLIES AND SCENT WARMERS COMPRISING SUCH MODULES, AND RELATED METHODS

(71) Applicant: Scentsy, Inc., Meridian, ID (US)

(72) Inventor: Brandon Juarez, Eagle, ID (US)

(73) Assignee: Scentsy, Inc., Meridian, ID (US)

( * ) Notice: Subject to any disclaimer, the term of this patent is extended or adjusted under 35 U.S.C. 154(b) by 0 days.

(21) Appl. No.: 14/301,149

(22) Filed: Jun. 10, 2014

(65) Prior Publication Data

US 2014/0290040 A1 Oct. 2, 2014

Related U.S. Application Data

(63) Continuation of application No. 13/160,842, filed on Jun. 15, 2011, now Pat. No. 8,772,675.

(51) Int. Cl.
*H05B 11/00* (2006.01)
*A61L 9/03* (2006.01)
*H05B 3/26* (2006.01)
(Continued)

(52) U.S. Cl.
CPC ............... *A61L 9/03* (2013.01); *F21V 33/0004* (2013.01); *H05B 3/26* (2013.01); *A61L 2209/12* (2013.01); *F21S 6/00* (2013.01); *F21S 8/035* (2013.01); *F21Y 2101/02* (2013.01); *F21Y 2103/025* (2013.01); *Y10T 29/49002* (2015.01); *Y10T 29/49083* (2015.01); *Y10T 29/49721* (2015.01)

(58) Field of Classification Search
USPC ............. 219/209, 433, 220, 438; 362/249.02, 362/249.01, 643, 96; 392/386, 390–5, 438, 392/429, 432–3
See application file for complete search history.

(56) References Cited

U.S. PATENT DOCUMENTS 5,651,942 A 7/1997 Christensen
5,903,710 A 5/1999 Wefler et al.
(Continued)

FOREIGN PATENT DOCUMENTS

CN 201304124 Y 9/2009
CN 201510547 U 6/2010
(Continued)

OTHER PUBLICATIONS

International Search Report for PCT/US2012/041391, mailed Feb. 27, 2013, 5 pages.
(Continued)

*Primary Examiner* — Shawntina Fuqua
(74) *Attorney, Agent, or Firm* — TraskBritt

(57) ABSTRACT

Modular assemblies for use with a scent warmer configured to heat a scented material and emit light comprise a lighting module and a heating module. The lighting module comprises at least one electrical light source. A male electrical connector is in electrical communication with and disposed on a first side of the at least one electrical light source. A female electrical connector is disposed on another side of the at least one electrical light source and in electrical communication with the male electrical connector. The heating module comprises a male electrical connector threadedly engaged and in electrical communication with the female electrical connector of the lighting module. A heating element is located at an end of the heating module opposing the male electrical connector and in electrical communication with the male electrical connector.

20 Claims, 7 Drawing Sheets

(51) Int. Cl.
*F21V 33/00* (2006.01)
*F21V 21/00* (2006.01)
*F21S 6/00* (2006.01)
*F21S 8/00* (2006.01)
*F21Y 101/02* (2006.01)
*F21Y 103/025* (2006.01)

(56) References Cited

U.S. PATENT DOCUMENTS

| | | | |
|---|---|---|---|
| 5,945,094 | A | 8/1999 | Martin et al. |
| 6,085,026 | A | 7/2000 | Hammons et al. |
| 6,106,786 | A | 8/2000 | Akahoshi |
| 6,354,710 | B1 | 3/2002 | Nacouzi |
| 6,478,440 | B1 | 11/2002 | Jaworski et al. |
| 6,527,418 | B1 | 3/2003 | Scherba |
| 6,627,857 | B1 | 9/2003 | Tanner et al. |
| 6,779,905 | B1 | 8/2004 | Mazursky et al. |
| 6,805,300 | B2 | 10/2004 | Munroe et al. |
| 6,917,754 | B2 | 7/2005 | Pedrotti et al. |
| 6,966,665 | B2 | 11/2005 | Limburg et al. |
| 7,046,919 | B2 | 5/2006 | Shimizu et al. |
| 7,121,686 | B1 | 10/2006 | Chu |
| 7,186,016 | B2 | 3/2007 | Jao |
| 7,246,919 | B2 | 7/2007 | Porchia et al. |
| 7,277,626 | B2 | 10/2007 | Pesu et al. |
| 7,318,659 | B2 | 1/2008 | Demarest et al. |
| 7,350,720 | B2 | 4/2008 | Jaworski et al. |
| 7,419,281 | B2 | 9/2008 | Porchia et al. |
| 7,455,444 | B2 | 11/2008 | Chien |
| 7,476,002 | B2 | 1/2009 | Wolf et al. |
| 7,481,571 | B2 | 1/2009 | Bistritzky et al. |
| 7,484,860 | B2 | 2/2009 | Demarest et al. |
| 7,503,668 | B2 | 3/2009 | Porchia et al. |
| 7,503,675 | B2 | 3/2009 | Demarest et al. |
| 7,543,957 | B1 | 6/2009 | Balazs et al. |
| 7,572,412 | B2 | 8/2009 | Yang |
| 7,611,253 | B2 | 11/2009 | Chien |
| 7,618,151 | B2 | 11/2009 | Abbondanzio et al. |
| 7,641,364 | B2 | 1/2010 | Abbondanzio et al. |
| 7,687,744 | B2 | 3/2010 | Walter et al. |
| 7,699,603 | B2 | 4/2010 | Furner et al. |
| 7,824,627 | B2 | 11/2010 | Michaels et al. |
| 7,839,068 | B2 | 11/2010 | Hayashi et al. |
| 7,932,482 | B2 | 4/2011 | Norwood et al. |
| 8,772,675 | B2 | 7/2014 | Juarez |
| 8,878,102 | B2 | 11/2014 | Juarez |
| 2005/0016985 | A1 | 1/2005 | Haas et al. |
| 2005/0184045 | A1 | 8/2005 | Shimizu et al. |
| 2005/0195600 | A1 | 9/2005 | Porchia et al. |
| 2006/0152946 | A1 | 7/2006 | Chien |
| 2007/0086199 | A1 | 4/2007 | Demarest et al. |
| 2008/0279731 | A1 | 11/2008 | Goreham et al. |
| 2009/0025567 | A1 | 1/2009 | Greenberg et al. |
| 2009/0073694 | A1 | 3/2009 | Scannell, Jr. |
| 2009/0196587 | A1 | 8/2009 | Cheung |
| 2009/0289047 | A1* | 11/2009 | Hisao ............................. 219/220 |
| 2010/0096376 | A1 | 4/2010 | Hsiao |
| 2010/0260646 | A1 | 10/2010 | Jorgensen |
| 2010/0270943 | A1 | 10/2010 | Cook |
| 2010/0290254 | A1 | 11/2010 | Howard et al. |
| 2011/0110092 | A1 | 5/2011 | Hsiao |
| 2011/0110118 | A1 | 5/2011 | Hsiao |
| 2011/0110824 | A1 | 5/2011 | Hsiao |
| 2011/0267821 | A1* | 11/2011 | Van De Ven et al. .... 362/249.02 |
| 2012/0024837 | A1* | 2/2012 | Thompson ................... 219/433 |
| 2012/0318779 | A1 | 12/2012 | Juarez |
| 2012/0318780 | A1 | 12/2012 | Juarez |

FOREIGN PATENT DOCUMENTS

| | | |
|---|---|---|
| DE | 202009005303 U1 | 8/2009 |
| DE | 202009014766 U1 | 3/2010 |
| EP | 0884078 | 12/1998 |
| JP | 11197226 A | 7/1999 |
| JP | 3146210 B1 | 3/2001 |
| JP | 2001327588 A | 11/2001 |
| JP | 2003310732 A | 11/2003 |
| WO | 2005074999 A1 | 8/2005 |
| WO | 2009027668 A1 | 3/2009 |
| WO | 2009027670 A1 | 3/2009 |
| WO | 2010062529 A2 | 6/2010 |
| WO | 2010135789 A1 | 12/2010 |

OTHER PUBLICATIONS

International Written Opinion for PCT/US2012/041391, mailed Feb. 27, 2013, 5 pages.
Letter Dated Nov. 18, 2013 from Lynn G. Foster to J. Jeffrey Gunn and Stephen E. Pulley with Enclosures; Candle Warmer "the original alternative to lighting a candle" Product Guide 2005, www.candlewarmers.com, 4 pages; color photograph.
Extended European Search Report for EP Application No. 11164677.4 dated Sep. 19, 2011, 5 pages.
International Search Report for International Application No. PCT/US2011/033629, dated Dec. 29, 2011, 6 pages.
International Written Opinion for International Application No. PCT/US2011/033629, dated Dec. 29, 2011, 4 pages.
International Preliminary Report on Patentability for International Application No. PCT/US2011/033629, dated Jan. 29, 2013, 5 pages.

* cited by examiner

ELECTRICAL LIGHTING AND HEATING MODULES, ASSEMBLIES AND SCENT WARMERS COMPRISING SUCH MODULES, AND RELATED METHODS

CROSS-REFERENCE TO RELATED APPLICATIONS

This application is a continuation of U.S. patent application Ser. No. 13/160,842, filed Jun. 15, 2011, now U.S. Pat. No. 8,772,675, issued Jul. 8, 2014, the disclosure of which is hereby incorporated herein in its entirety by this reference. The subject matter of this application is also related to the subject matter of co-pending U.S. patent application Ser. No. 13/092,697, which was filed Apr. 22, 2011 and is entitled "Scent Warmers Having Non-Incandescent Heating and Light Emitting Devices and Related Methods" and U.S. patent application Ser. No. 13/160,790, filed Jun. 15, 2011, now U.S. Pat. No. 8,878,102, issued Nov. 11, 2014, which is entitled "Base Structures, Scent Warmers Including Such Base Structures, and Related Methods," the disclosure of each of which is incorporated herein in its entirety by this reference.

FIELD

Embodiments of the disclosure relate generally to scent warmers. More particularly, embodiments of the disclosure relate to scent warmers including lighting modules and heating modules.

BACKGROUND

For many years, candles made from scented wax have been used to create an aroma in a surrounding area. Traditionally, candles include a wick that may be lit by a flame. The burning wick melts the wax near the wick and pulls the liquid wax, along with the scents included in the wax, up into the wick by capillary action or absorption. The flame burns the scented wax, and an aroma is released into the area surrounding the candle. The flame of the traditional candle also produces light, which is often regarded as desirable for creating a pleasing ambience or for providing energy efficient light, for example. While light and an aroma are produced by candles, traditional candles produce some risks and hazards, including a risk of burns, fires, and smoke.

Recently, scent warmers have been used, as an alternative to candles, to heat scented wax or scented oil. Scent warmers are often referred to as flameless candles or wickless candles. Some scent warmers release the aroma from the scented wax or oil without the use of a flame. For example, scent warmers may include a base that houses an incandescent light bulb acting as a heat source. The incandescent light bulb is positioned inside the base under a plate holding the scented wax or oil. The incandescent light bulb heats the bottom of the plate primarily through radiation and convection. The plate, in turn, heats the wax or oil, thus releasing the scent into the surrounding area by increasing the rate of evaporation or dissipation of the scented material. Such scent warmers are generally safer than traditional candles because of the absence of a flame. However, incandescent light bulbs are generally seen as inefficient and may include their own disadvantages. For example, incandescent bulbs may need frequent replacement, adding to the cost of operating the scent warmer.

Other scent warmers use a resistive heating element, rather than an incandescent light bulb, to heat scented wax or oil. Such scent warmers may include a plate for holding scented wax or oil with a resistive heating element attached to the bottom of the plate. The heating element heats the plate primarily by conduction, and the plate transfers the heat to the scented wax or oil, thereby releasing an aroma into the surrounding area. However, such scent warmers do not produce light.

Still other scent warmers, such as those disclosed in U.S. patent application Ser. No. 13/092,697, which was filed Apr. 22, 2011 and is entitled "Scent Warmers Having Non-Incandescent Heating and Light Emitting Devices and Related Methods," may produce light by including light sources, such as light emitting diodes (LEDs) or compact fluorescent lamps (CFLs) within a base, which may include holes, translucent portions, or transparent portions that allow light to pass from the base interior to the base exterior.

The constituent parts of any of the foregoing scent warmers, however, may not be easily accessible or removable, which may increase the difficulty or complexity of replacing such constituent parts of the scent warmers when those constituent parts are defective, are broken, or have exceeded their useful life.

BRIEF DESCRIPTION OF THE DRAWINGS

While the specification concludes with claims particularly pointing out and distinctly claiming that which is regarded as the present invention, various features and advantages of embodiments of the disclosure may be more readily ascertained from the following description of embodiments of the disclosure when read in conjunction with the accompanying drawings, in which:

DETAILED DESCRIPTION

The illustrations presented herein are not meant to be actual views of any particular scent warmer, module for use with a scent warmer, or components or portions thereof, but are merely idealized representations that are employed to describe certain disclosed embodiments. Thus, the drawings are not necessarily to scale and relative dimensions may have been exagaerated for the sake of clarity or simplicity. Additionally, elements common between figures may retain the same or similar numerical designation.

Embodiments of the disclosure relate generally to scent warmers. More particularly, embodiments of the disclosure relate to scent warmers including lighting modules and heating modules that may facilitate simple and easy assembly of scent warmers and replacement of lighting and heating modules for use with scent warmers.

As used herein, any directional term (e.g., upper, lower, over, under, side, top, bottom, etc.) refers to a direction relative to the device when the device is used during normal operation. By way of non-limiting example, an upper portion of a scent warmer is the upper portion while the scent warmer is in an orientation for use, and used to warm scented material.

As used herein, the term "module" means and includes any independently operable unit that may be a part of an overall structure of an assembly. For example, a module may include a unit for providing light, a unit for providing heat, or a unit for providing both light and heat in a scent warmer assembly.

As used herein, the term "translucent" means and includes any material that exhibits less than 100% opacity. In other words, a translucent material permits at least some light to pass therethrough. For example, a translucent material may transmit and diffuse light so that objects cannot be seen clearly therethrough or may be completely transparent to visible light (i.e., transmitting light without appreciable scattering) so that objects can be seen clearly therethrough.

Figure 1:
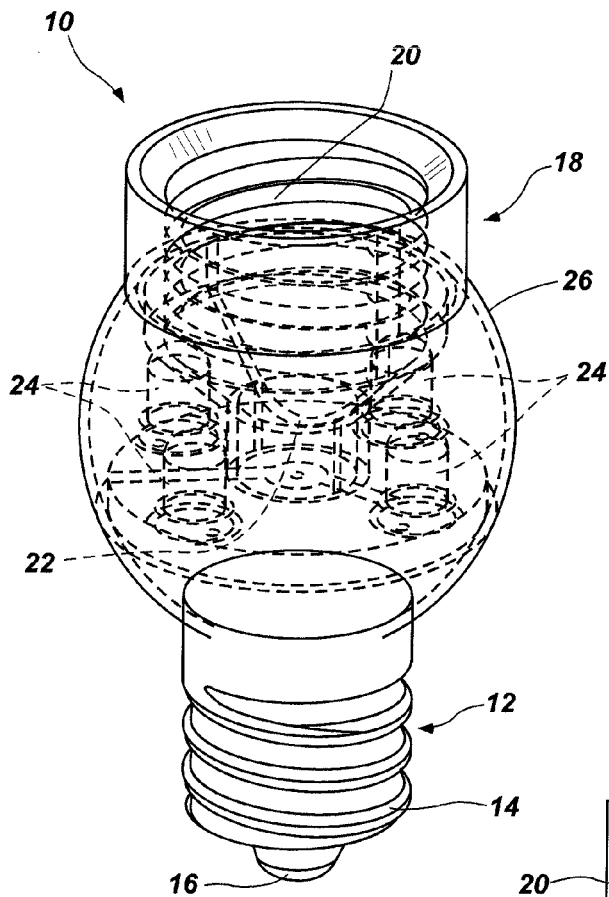
FIG. 1 is a perspective view of a lighting module that may be used with a scent warmer.
Figure 2:
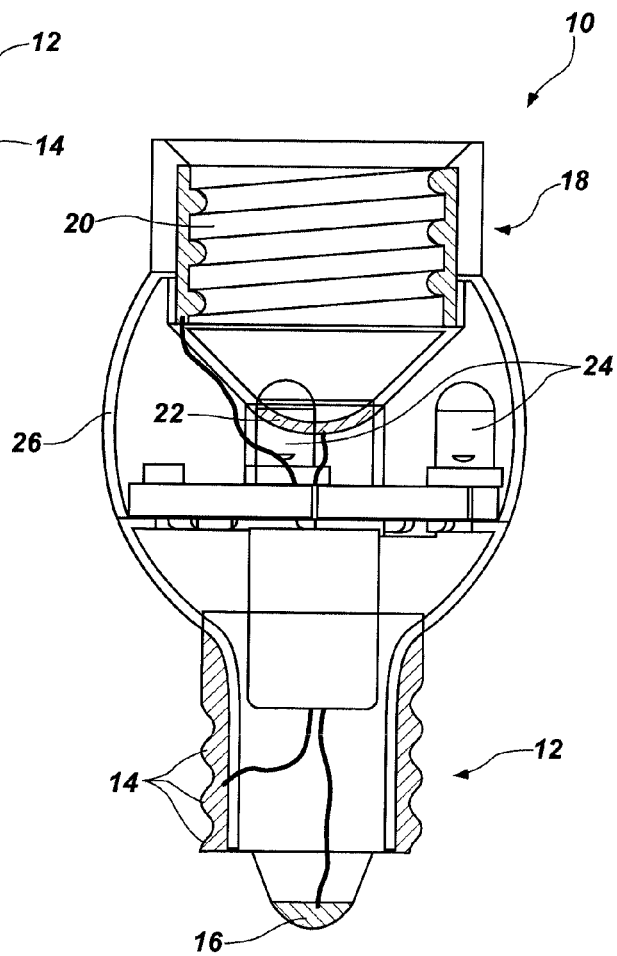
FIG. 2 depicts a cross-sectional view of the lighting module of FIG. 1.

Referring to FIGS. 1 and 2, a perspective view and a cross-sectional view of a lighting module 10 that may be used with a scent warmer are shown, respectively. The lighting module 10 comprises a male threaded electrical connector 12. The male threaded electrical connector 12 may be disposed at a lower portion of the lighting module 10. Thus, the lighting module 10 may be configured for threaded engagement with a female threaded electrical connector disposed below the lighting module 10. The male threaded electrical connector 12 may comprise at least one helically extending protrusion 14 configured to threadedly engage and electrically communicate with a female threaded electrical connector and at least one contact 16 configured to electrically communicate with a contact of the female threaded electrical connector to form a closed electrical path. At least a portion of the male threaded electrical connector 12 may comprise an electrically conductive material and may be configured to receive electrical power from an electrical power source.

The male threaded electrical connector 12 may comprise a male Edison screw fitting. Standards for Edison screw fittings may be obtained, for example, from the American National Standards Institute (ANSI). Edison screw fittings may specifically conform to ANSI Standard C81.61-2009, which sets forth specifications for bases or caps for electric lamps. Generally, Edison screw fittings comprise a right-hand threading that forms one of the contacts for a circuit and a bottom center portion that forms the other contact to close the circuit. By way of example, the male threaded electrical connector 12 may comprise a standard E5, E5.5, E10, E11, E12, E14, E17, E26, E27, E39, or E40 Edison screw fitting, where the numbers following "E" may correspond to the diameter of the Edison screw fitting in millimeters. As a specific, nonlimiting example, the male threaded electrical connector 12 may comprise a standard E11 Edison screw fitting, which may correspond to a standard candelabra size Edison screw fitting as used in Europe. As another specific, nonlimiting example, the male threaded electrical connector 12 may comprise a standard E27, also known in the art as a standard "ES," Edison screw fitting, which may correspond to a medium, or standard size, light bulb Edison screw fitting as used in Europe.

The lighting module 10 may further comprise a female threaded electrical connector 18. The female threaded electrical connector 18 may be disposed at an upper portion of the lighting module 10. Thus, the lighting module 10 may be configured to receive a male threaded electrical connector from above the lighting module 10. The female threaded electrical connector 18 may comprise at least one helically extending recess 20 configured to threadedly engage and electrically communicate with a male threaded electrical connector and at least one contact 22 configured to communicate with a contact of the male threaded electrical connector 12 to form a closed electrical path. At least a portion of the female threaded electrical connector 18 may comprise an electrically conductive material and may be in electrical communication with the male threaded electrical connector 12. For example, a pass-through electrical connection may provide electrical communication between the male threaded electrical connector 12 and the female threaded electrical connector 18. Thus, a single power source may provide electrical power to both the male threaded electrical connector 12 and the female threaded electrical connector 18.

The female threaded electrical connector 18 may comprise a female Edison screw fitting. As a specific, nonlimiting example, the female threaded electrical connector 18 may comprise a standard E11 Edison screw fitting, which may correspond to a standard candelabra size Edison screw fitting as used in Europe. As another specific, nonlimiting example, the female threaded electrical connector 18 may comprise a standard E27, also known in the art as a standard "ES," Edison screw fitting, which may correspond to a medium, or standard size, light bulb Edison screw fitting as used in Europe. The female threaded electrical connector 18 may comprise the same size Edison screw fitting as the male threaded electrical connector 12 in some embodiments. In other embodiments, the female threaded electrical connector 18 may comprise a different size Edison screw fitting from the male threaded electrical connector 12.

The lighting module 10 may comprise at least one electrical light source 24 interposed between the male threaded electrical connector 12 and the female threaded electrical connector 18. Thus, the male threaded electrical connector 12 may be disposed on a first, lower side of the electrical light source 24, and the female threaded electrical connector 18 may be disposed on another, upper side of the electrical light source 24 opposing the first, lower side on which the male threaded electrical connector 12 is disposed. As shown in FIGS. 1 and 2, a plurality of electrical light sources 24 may be disposed in an array between the male threaded electrical connector 12 and the female threaded electrical connector 18. For example, four electrical light sources 24 may be distributed in a substantially uniformly spaced array around a periphery of the lighting module 10. The electrical light sources 24 may be in electrical communication with the male threaded electrical connector 12. For example, a pass-through electrical connection may provide electrical communication between the male threaded electrical connector 12 and the electrical light sources 24. Thus, a single power source may provide electrical power to the male threaded electrical connector 12, the female threaded electrical connector 18, and the electrical light sources 24.

The lighting module 10 may include a cover member 26. The cover member 26 may be used to structurally connect the male threaded electrical connector 12 to the female threaded electrical connector 18. The cover member 26 may comprise an at least substantially hollow member that defines an inner cavity in which the electrical light sources 24 may be disposed. At least a portion of the cover member 26 may comprise a translucent material. By way of example, the cover member 26 may comprise a translucent polymer material. Accordingly, at least some light emitted by the electrical light sources 24 may pass through the cover member 26. The cover member 26 may be transparent in some embodiments. In other embodiments, the cover member 26 may diffuse light emitted by the electrical light sources 24 such that only some of the light passes through the cover member 26. The cover member 26 may also include holes formed therethrough, which may enable light emitted by the electrical light sources 24 to pass from the internal cavity of the cover member 26 to an exterior of the cover member 26. The translucent material of the cover member 26 may be colored in some embodiments. For example, the translucent material of the cover member 26 may absorb at least some wavelengths of visible light while permitting other wavelengths of light to pass through, thereby imparting a desired hue to the light that passes through the cover member 26. In other embodiments, the translucent material of the cover member 26 may be patterned with opaque designs, or with two or more colors of translucent material.

Figure 3:
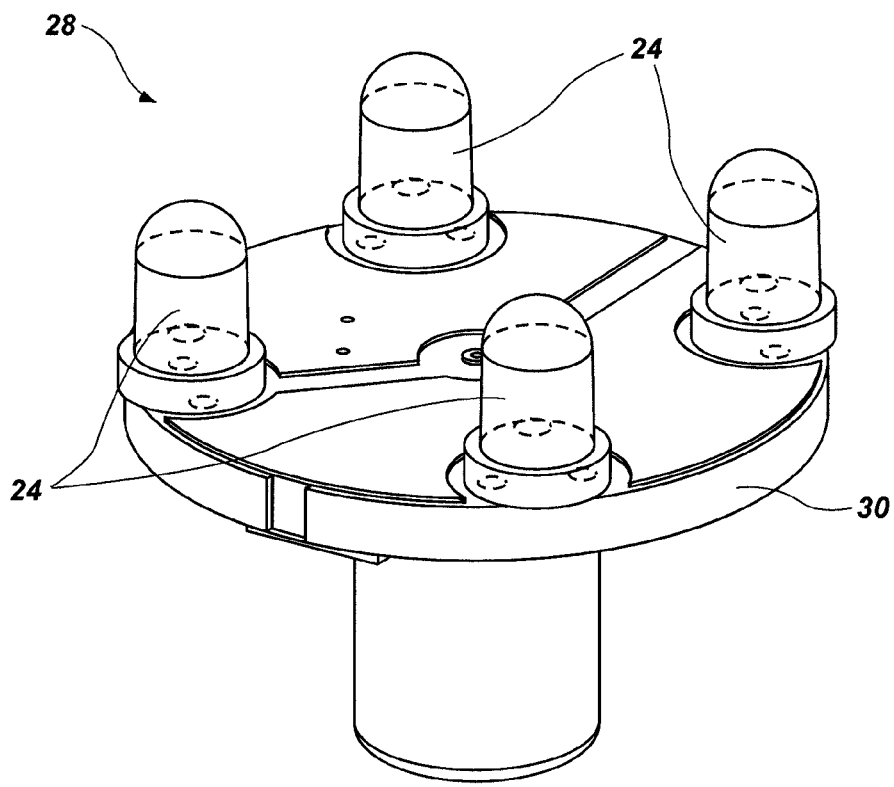
FIG. 3 illustrates a perspective view of an assembly of electrical light sources that may be used with the lighting module of FIG. 1.

Referring to FIG. 3, a perspective view of an assembly 28 of electrical light sources 24 that may be used with the lighting module 10 of FIG. 1 is shown. The electrical light sources 24 may be provided in an array on a carrier substrate 30, such as, for example, a printed circuit board, which may structurally connect and support the electrical light sources 24. The electrical light sources 24 may be filamentless in some embodiments. For example, the electrical light sources 24 may comprise light emitting diodes (LEDs), compact fluorescent lamps (CFLs), or electroluminescent devices (e.g., powder phosphor-based electroluminescent devices). In other embodiments, the electrical light sources 24 may comprise a filament light source, such as, for example, an incandescent lamp. In embodiments where the electrical light sources 24 comprise LEDs, the electrical light sources 24 may comprise single-colored LEDs or LEDs of a design capable of changing color. For example, the electrical light sources 24 may comprise an array of LEDs capable of emitting red, green, and blue light, alone or in combination with one another, sometimes referred to as "RGB LEDs." Thus, the electrical light sources 24, the cover member 26 (see FIGS. 1 and 2), or both may act to impart a hue to light emitted by the lighting module 10 (see FIGS. 1 and 2).

Figure 4:
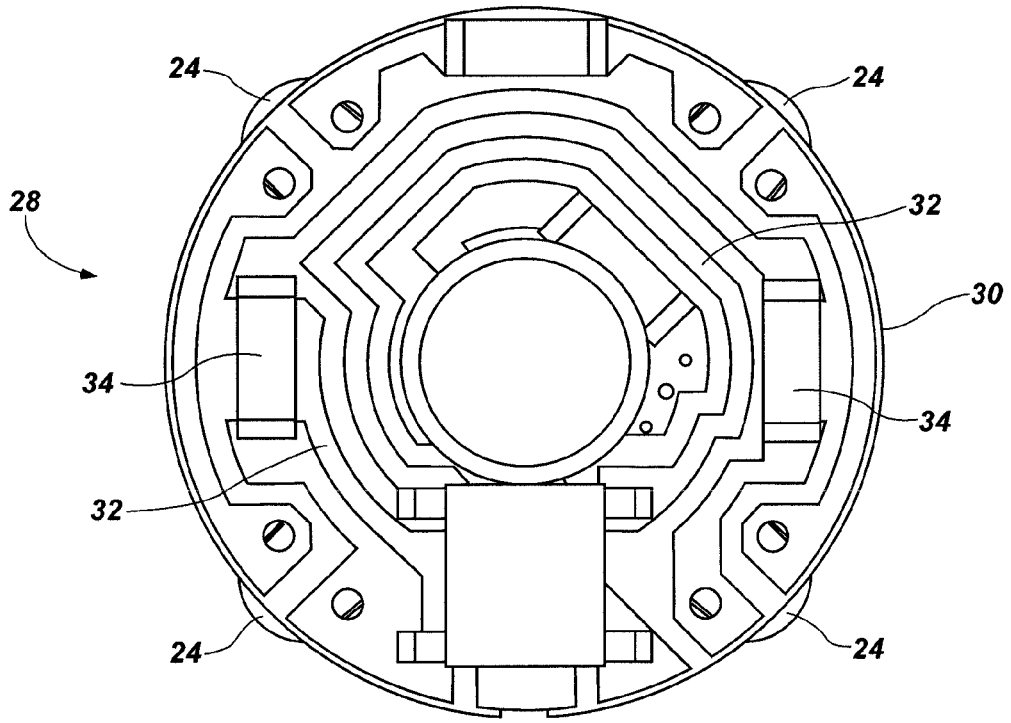
FIG. 4 is a plan view from below the assembly of electrical light sources of FIG. 3 depicting circuitry that may be used with the assembly of electrical light sources.

Referring to FIG. 4, a plan view from below the assembly 28 of electrical light sources 24 of FIG. 3 depicts circuitry that may be used with the assembly of electrical light sources. The carrier substrate 30 may comprise an electrically conductive material configured to electrically communicate with the male threaded electrical connector 12 of a lighting module 10 (see FIGS. 1 and 2) and with the electrical light sources 24. For example, the carrier substrate 30 may include metal traces 32 disposed on a surface thereof in electrical communication with the electrical light sources 24 and configured to electrically communicate with the male threaded electrical connector 12 of a lighting module 10 (see FIGS. 1 and 2). The carrier substrate 30 may also comprise circuitry 34 configured to control at least one of intensity, flickering, and coloring of visible light emitted by the electrical light sources 24. For example, the carrier substrate 30 may comprise circuitry 34 in electrical communication with the electrical light sources 24 via the traces 32 that may be configured to change at least one of intensity, flickering, and coloring of electrical light sources 24 comprising LEDs in response to a user input. In addition or in the alternative, the circuitry 34 may be configured to convert Alternating Current (AC) electrical power to Direct Current (DC) electrical power, such a circuit being known in the art as an AC rectifier circuit. As a specific, nonlimiting example, the circuitry 34 may enable a user to selectively change the electrical light sources 24 from emitting substantially constant white light of a first intensity to emitting flickering yellow light of a second, dimmer intensity. In another non-limiting example, circuitry 34 may comprise one or more power conversion modules to reduce household power (e.g., current) input to electrical light sources 24, or to female threaded electrical connector 18, or both, as desired.

Figure 5:
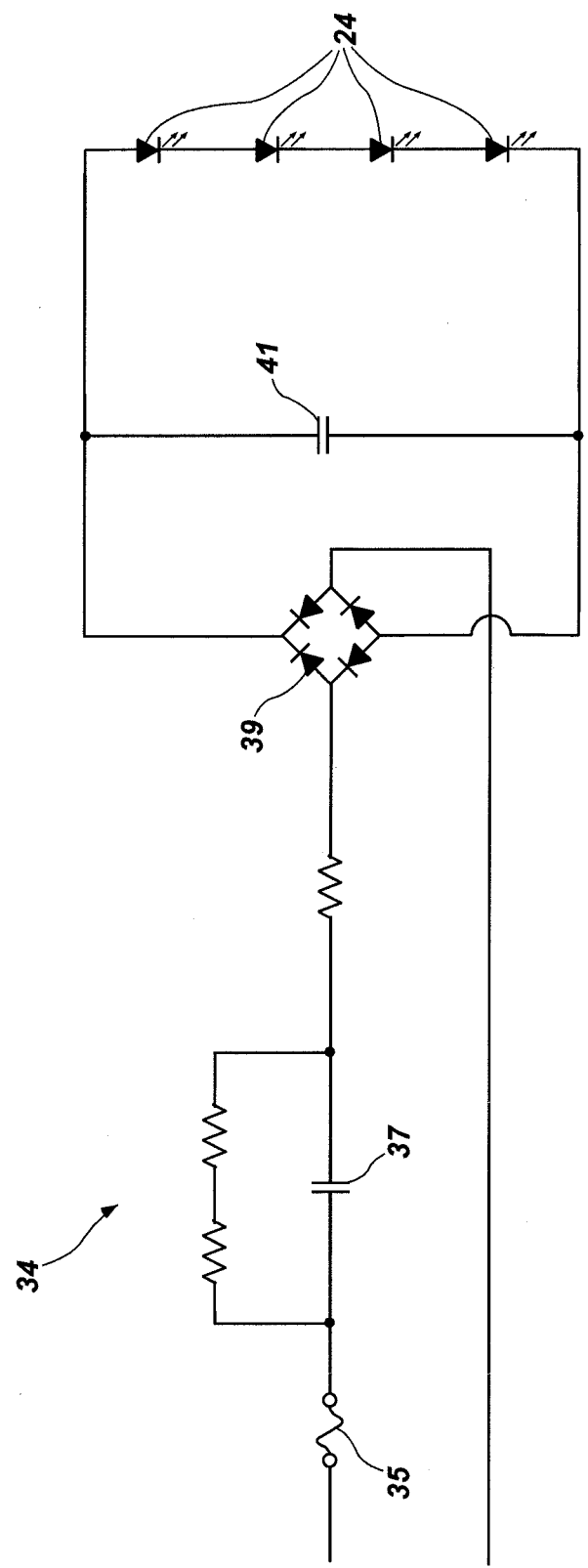
FIG. 5 is a circuit diagram of a circuit that may be used with the assembly of electrical light sources of FIG. 3.

Referring to FIG. 5, one embodiment of a circuit diagram of a circuit 34 that may be used with the assembly 28 of electrical light sources 24 of FIG. 3 is shown. As depicted, the circuit 34 may comprise a fuse 35 configured to prevent excessive and potentially damaging current levels from flowing through the circuit 34, for example, to electrical light sources 24. For example, the fuse 35 may comprise a 200 mA fuse. The circuit 34 may also comprise a parallel resistor-capacitor (RC) circuit 37. For example, the parallel RC circuit 37 may comprise resistors having a total resistance of 660 kΩ in parallel with capacitors having a total capacitance of 0.33 μF. The capacitor in the parallel RC circuit 37 may diminish the amplitude and fluctuation of current (e.g., fluctuation of direct current, fluctuation of alternating current, or simply high amplitude portions of alternating current) flowing through the circuit 34, while the resistors may enable the capacitor to discharge after the circuit 34 has been disconnected from an electrical power source. Additional resistors, capacitors, and other electrical components may be used, as needed or desired. The circuit 34 may include a diode bridge 39 configured to provide the same polarity output regardless of the polarity of input to the circuit 34. By including a reservoir capacitor 41 in parallel with the electrical light sources 24, the circuit 34 may act as an AC rectifier due to the smoothing provided by the reservoir capacitor 41 in connection with the diode bridge 39.

Figure 6:
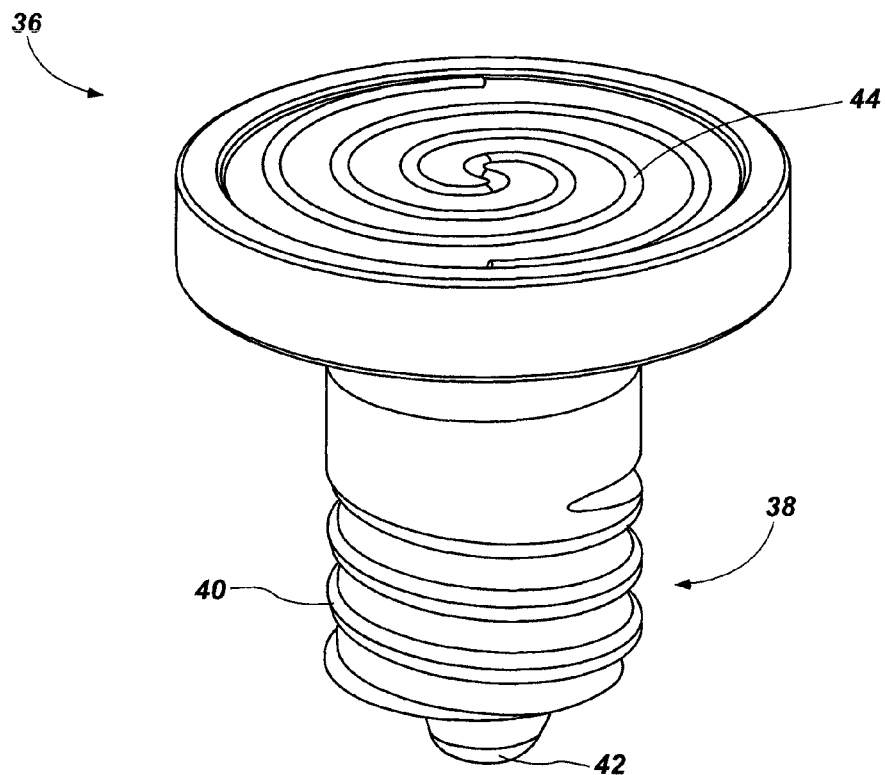
FIG. 6 illustrates a perspective view of a heating module that may be used with a scent warmer.
Figure 7:
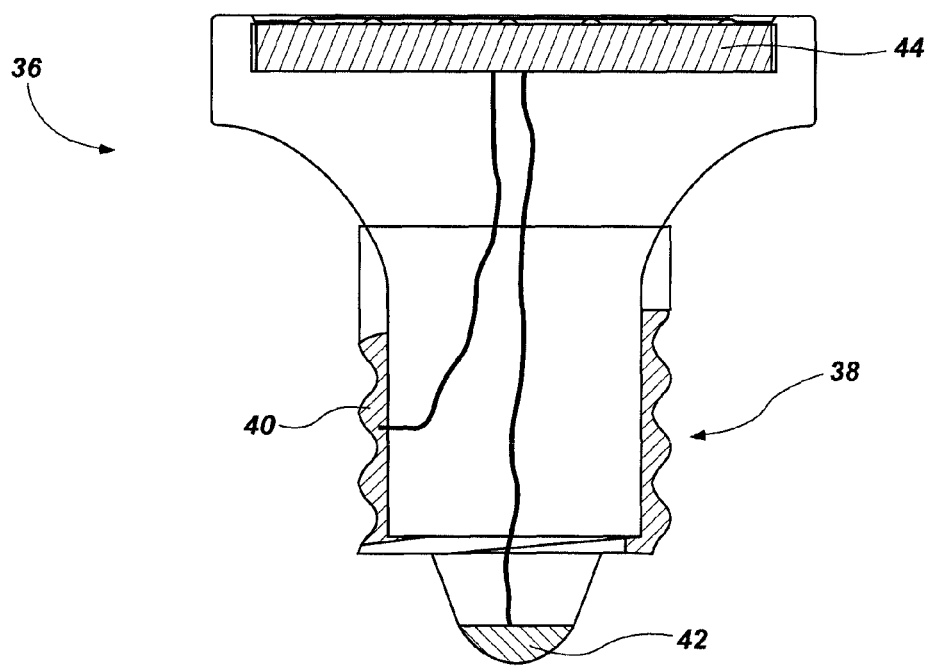
FIG. 7 is a cross-sectional view of the heating module shown in FIG. 6.

Referring to FIGS. 6 and 7, a perspective view and a cross-sectional view of a heating module 36 that may be used with a scent warmer are shown, respectively. The heating module 36 may comprise a male threaded electrical connector 38 configured for threaded engagement with a female threaded electrical connector 18 of a lighting module 10 (see FIGS. 1 and 2). The male threaded electrical connector 38 may be disposed at a lower portion of the heating module 10. The male threaded electrical connector 12 may comprise at least one helically extending protrusion 40 configured to threadedly engage and electrically communicate with the helically extending recess 20 of a female threaded electrical connector 18 and at least one contact 42 configured to electrically communicate with the contact 22 of the female threaded electrical connector 18 (see FIGS. 1 and 2) to form a closed electrical path. At least a portion of the male threaded electrical connector 38 may comprise an electrically conductive material and may be configured to receive electrical power from the female threaded electrical connector 18 (see FIGS. 1 and 2).

The male threaded electrical connector 38 may comprise a male Edison screw fitting. As a specific, nonlimiting example, the male threaded electrical connector 38 may comprise a standard E11 Edison screw fitting, which may correspond to a standard candelabra size Edison screw fitting as used in Europe. As another specific, nonlimiting example, the male threaded electrical connector 38 may comprise a standard E27, also known in the art as a standard "ES," Edison screw fitting, which may correspond to a medium, or standard, size light bulb Edison screw fitting as used in Europe. The male threaded electrical connector 38 may comprise the same size Edison screw fitting as the female threaded electrical connector 18 of a lighting module 10 (see FIGS. 1 and 2). Thus, the heating module 36 may be configured for mechanical and electrical connection to a lighting module 10 (see FIGS. 1 and 2).

The heating module 36 may comprise a heating element 44. The heating element 44 may be disposed at an upper portion of the heating module 36 above the male threaded electrical connector 38. Thus, the heating element 44 may be located at an end of the heating module 36 opposing the male threaded electrical connector 38. The heating element 44 may be electrically connected to the male threaded electrical connector 38 and configured to receive electrical power therefrom. The heating element 44 may comprise, for example, a resistive element (e.g., a ceramic element or a filament-type element), an infrared element, a Peltier-type thermocouple element, or inductive heating element, which may heat a receptacle having a ferrous lining or insert.

The heating element 44 may be configured to heat to a temperature suitable for warming a scented material. The heating element 44 may also be configured to only heat to a temperature sufficiently low that the scented material being warmed does not ignite and that the heating module 36 and any other devices near the heating element 44 retain structural integrity (i.e., do not experience catastrophic failure due to temperature-induced weakening of the materials from which they are formed). For example, the heating element 44 may be configured to heat to a temperature of between about 45° C. and 70° C. As a continuing example, the heating element 44 may be configured to heat to a temperature of between about 50° C. and about 60° C. In one nonlimiting example, heating module 36 may incorporate a power conversion module to reduce household power (e.g., current) input. Another approach is incorporation of a thermocouple in the circuit to remove power from heating element 44 when the temperature becomes undesirably high.

Figures 8, 9:
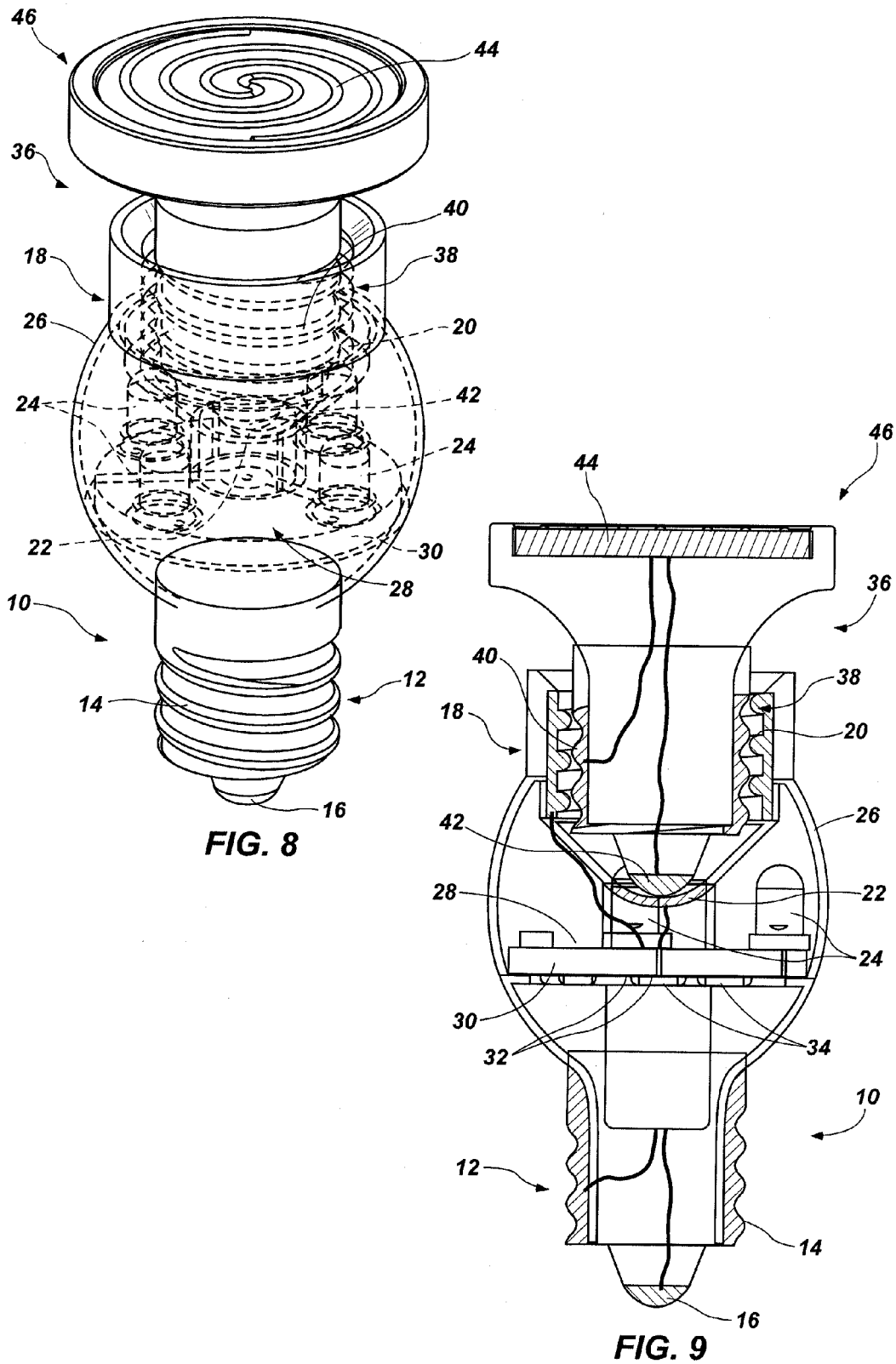
FIG. 8 depicts a perspective view an assembly of the lighting module of FIGS. 1 and 2 with the heating module of FIGS. 6 and 7.
FIG. 9 illustrates a cross-sectional view of the assembly of FIG. 8.

Referring to FIGS. 8 and 9, a perspective view and a cross-sectional view of an assembly 46 of the lighting module 10 of FIGS. 1 and 2 with the heating module 36 of FIGS. 6 and 7 are shown, respectively. The male threaded electrical connector 38 of the heating module 36 may be threadedly engaged with the female threaded electrical connector 18 of the lighting module 10. Thus, the assembly 46 may be configured to emit both light and heat using the lighting module 10 and the heating module 36, respectively.

When assembling the assembly 46, the heating module 36 may be positioned over the lighting module 10, and the male threaded electrical connector 38 of the heating module 36 may be aligned with the female threaded electrical connector 18 of the lighting module 10. The heating module 36 may be simultaneously lowered and rotated with respect to the lighting module 10. Thus, the helically extending protrusion 40 of the male threaded electrical connector 38 of the heating module 36 may engage with the helically extending recess 20 of the female threaded electrical connector 18 of the lighting module 10. As the male threaded electrical connector 38 of the heating module 36 proceeds downwardly into the female threaded electrical connector 18 of the lighting module 10, the contact 42 of the male threaded electrical connector 38 of the heating module 36 may abut the contact 22 of the female threaded electrical connector 18 of the lighting module 10 to form a closed electrical path. For example, the electrical connection thus formed may comprise a pass-through electrical connection. Thus, electrical power provided to the male threaded electrical connector 12 of the lighting module 10 may be transmitted to both the lighting module 10 and the heating module 36, and the components thereof. For example, a single electrical power source may transmit electrical power to the male threaded electrical connector 12 of the lighting module 10, the electrical light sources 24 of the lighting module 10, the female threaded electrical connector 18 of the lighting module 10, the male threaded electrical connector 38 of the heating module 36, and the heating element 44 of the heating module 36.

Figure 10:
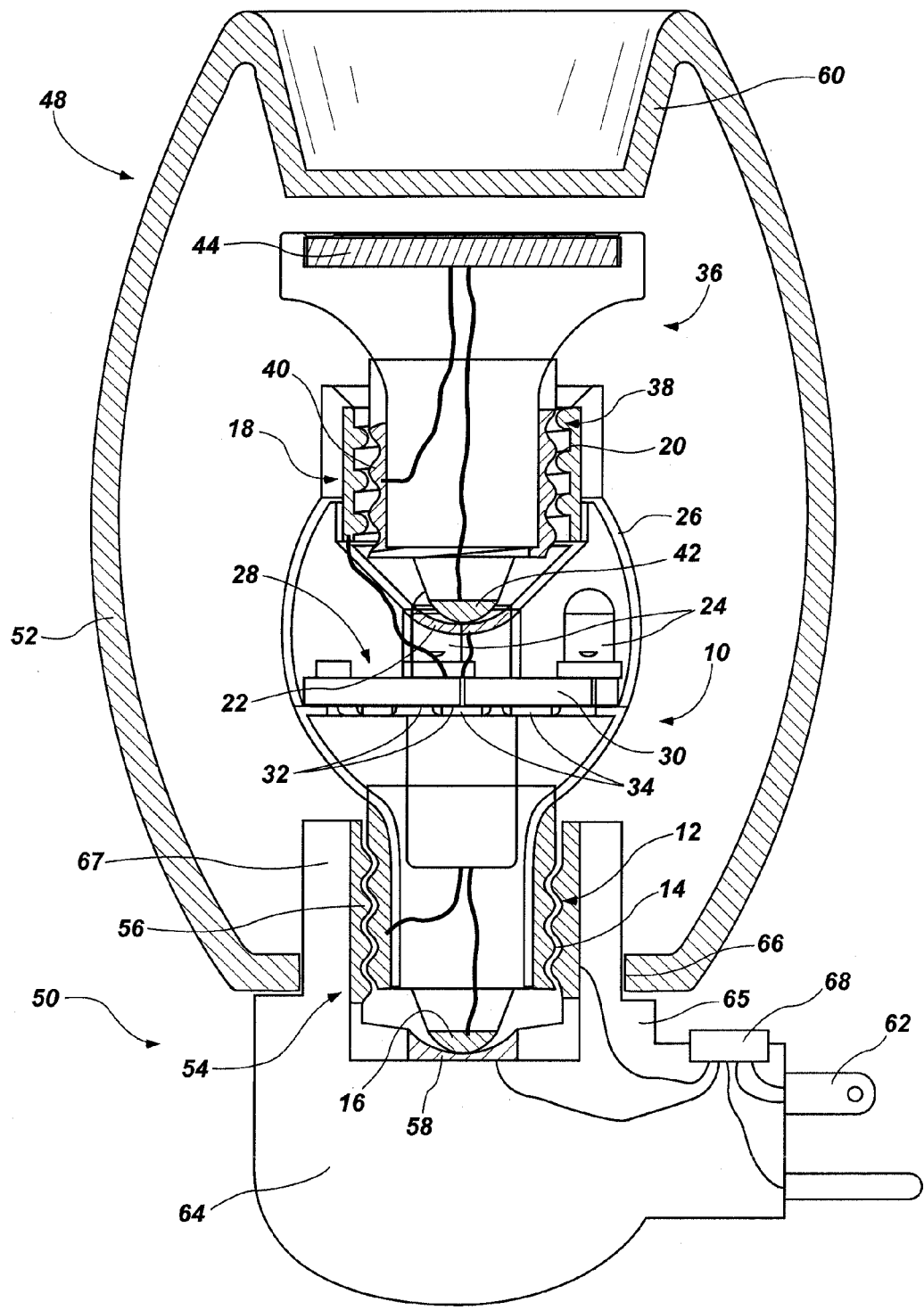
FIG. 10 depicts simplified a cross-sectional view of a scent warmer.

Referring to FIG. 10, a simplified cross-sectional view of a scent warmer 48 is shown. The scent warmer 48 may comprise a base structure 50. The base structure 50 may comprise an at least substantially hollow portion 52, which may be configured to receive at least one lighting module 10 and at least one heating module 36 at least partially therein. The at least substantially hollow portion 52 may be configured to receive a plurality of lighting modules 10 in combination with a heating module 36 therein to form a stacked assembly in some embodiments. The at least substantially hollow portion 52 may define a cavity in which a lighting module 10 assembled with a heating module 36, as described previously in connection with FIGS. 7 and 8, may be disposed. Thus, at least one lighting module 10 and at least one heating module 36 may be at least partially contained within the at least substantially hollow lower portion 52 of the base structure 52.

The at least substantially hollow portion 52 may comprise a translucent material. By way of example, the cover member 26 may comprise a translucent ceramic material. Accordingly, at least some light emitted by a lighting module 10 within the at least substantially hollow portion 52 may pass through the at least substantially hollow lower portion 52. The at least substantially hollow portion 52 may be transparent in some embodiments. In other embodiments, the at least substantially hollow portion 52 may diffuse light emitted by the lighting module 10 such that only some of the light passes through the at least substantially hollow portion 52. The translucent material of the at least substantially hollow portion 52 may be colored in some embodiments. For example, the translucent material of the at least substantially hollow portion 52 may absorb at least some wavelengths of visible light while permitting other wavelengths of light to pass through, thereby imparting a desired hue to the light that passes through the at least substantially hollow portion 52. In other embodiments, the translucent material of the at least substantially hollow portion 52 may be patterned with opaque designs, or with two or more colors of translucent material.

The base structure 50 may comprise a female threaded electrical connector 54. The female threaded electrical connector 54 may be disposed at a lower portion of the base structure 50. Thus, the base structure 50 may be configured to receive a male threaded electrical connector 12 of a lighting module 10, a male threaded electrical connector 38 of a heating module 36, or both in embodiments where the base structure comprises a plurality of female threaded electrical connectors 54. The female threaded electrical connector 54 may comprise at least one helically extending recess 56 configured to threadedly engage and electrically communicate with a helically extending protrusion 14 of a male threaded electrical connector 12 of a lighting module 10, a helically extending protrusion 40 of a male threaded electrical connector 38 of a heating module 36, or both. In addition, the female threaded electrical connector 38 may include at least one contact 58 configured to communicate with a contact 16 of a male threaded electrical connector 12 of a lighting module 10, a contact 42 of a male threaded electrical connector 38 of a heating module 36, or both to form a closed electrical path. At least a portion of the female threaded electrical connector 54 may comprise an electrically conductive material and may be in electrical communication with the male threaded electrical connector 12 of a lighting module 10 or the male threaded electrical connector 38 of a heating module 36. For example, a pass-through electrical connection may provide electrical communication between the male threaded electrical connector 12 of a lighting module 10, the male threaded electrical connector 38 of a heating module 36, and the female threaded electrical connector 54 of the base structure 50. Thus, a single power source may provide electrical power to the base structure 50, a lighting module 10 connected to the base structure 50, and a heating module 36 connected to the lighting module 10. In other words, a single power source may provide electrical power for the assembled scent warmer 48.

The female threaded electrical connector 54 of the base structure 50 may comprise a female Edison screw fitting. As a specific, nonlimiting example, the female threaded electrical connector 54 may comprise a standard E11 Edison screw fitting, which may correspond to a standard candelabra size Edison screw fitting as used in Europe. As another specific, nonlimiting example, the female threaded electrical connector 54 may comprise a standard E27, also known in the art as a standard "ES," Edison screw fitting, which may correspond to a medium, or standard, size light bulb Edison screw fitting as used in Europe. The female threaded electrical connector 54 of the base structure 50 may comprise the same size Edison screw fitting as the male threaded electrical connector 12 of the lighting module 10, the female threaded electrical connector 18 of the lighting module 10, and the male threaded electrical connector 38 of the heating module 36 in some embodiments. Thus, each of the lighting module 10, the heating module 36, and the base structure 50 may interchangeably connect with one another using their respective male and female threaded electrical connectors 12, 18, 38, and 54. In other embodiments, at least one of the female threaded electrical connector 54 of the base structure 50, the male threaded electrical connector 12 of the lighting module 10, the female threaded electrical connector 18 of the lighting module 10, and the male threaded electrical connector 38 of the heating module 36 may comprise a different size Edison screw fitting from at least another of the female threaded electrical connector 54 of the base structure 50, the male threaded electrical connector 12 of the lighting module 10, the female threaded electrical connector 18 of the lighting module 10, and the male threaded electrical connector 38 of the heating module 36. In addition, the base structure 50 may comprise a plurality of female threaded electrical connectors 54 in some embodiments, enabling a plurality of heating and lighting modules 36 and 10 (whether assembled together or not) to be disposed in the cavity of the at least substantially hollow portion 52.

The base structure 50 may comprise a receptacle 60 disposed over the at least substantially hollow portion 52 for supporting a scented material during use of the scent warmer 48. The receptacle 60 may comprise, for example, an upwardly facing cup-shaped portion in which a scented material may be disposed. The receptacle 60 may comprise the same material as the substantially hollow lower portion 52 and may be formed integrally with the substantially hollow lower portion 52 in some embodiments. Thus, the substantially hollow lower portion 52 and the receptacle 60 may form an integral structure.

The base structure 50 may comprise an electrical power source interface 62, such as, for example, a standard electrical power plug, in electrical communication with the female threaded electrical connector 54 of the base structure 50. The electrical power source interface 62 may extend from a support member 64 of the base structure 50. The female threaded electrical connector 54 of the base structure 50 may be disposed in the support member 64. In addition, the at least substantially hollow portion 52 may be disposed over, and rest on, the support member 64. Thus, when assembling the scent warmer 48, a heating module 36 may be threadedly engaged with a lighting module 10, which may be threadedly engaged with the female threaded electrical connector 54 disposed in the support member 64. A hole 66 formed in the bottom of at least substantially hollow portion 52 may be positioned over and aligned with the assembly of the heating module 36, the lighting module 10, and the support member 64. The at least substantially hollow lower portion 52 may be lowered, and the assembly of the heating module 36, the lighting module 10, and the support member 64 may be at least partially positioned within the cavity defined by the at least substantially hollow portion 52. The at least substantially hollow portion 52 may rest on and be supported by the support member 64, for example on an annular shoulder 65 surrounding protrusion 67 surrounding female threaded electrical connector 54. The electrical power source interface 62 may be rigidly connected to the support member 64. Thus, the scent warmer 48 may be configured to be supported by an electrical power source, such as, for example, an electrical power socket.

The base structure 50 may optionally comprise a user control interface 68. The user control interface 68 may be configured to receive input from a user to alter the operation of the scent warmer 48. For example, the user control interface 68 may comprise a switch that may be used to open and close the electrical path from the electrical power source interface 62 to the female threaded electrical connector 54 of the base structure and the other components in electrical communication therewith. Thus, the user control interface 68 may enable a user to turn the scent warmer 48 on and off. In addition, the user control interface 68 may be configured to change at least one of intensity of light emitted by the lighting module 10, color of light emitted by the lighting module 10, and flickering of light emitted by the lighting module 10 in response to a user input.

Figure 11:
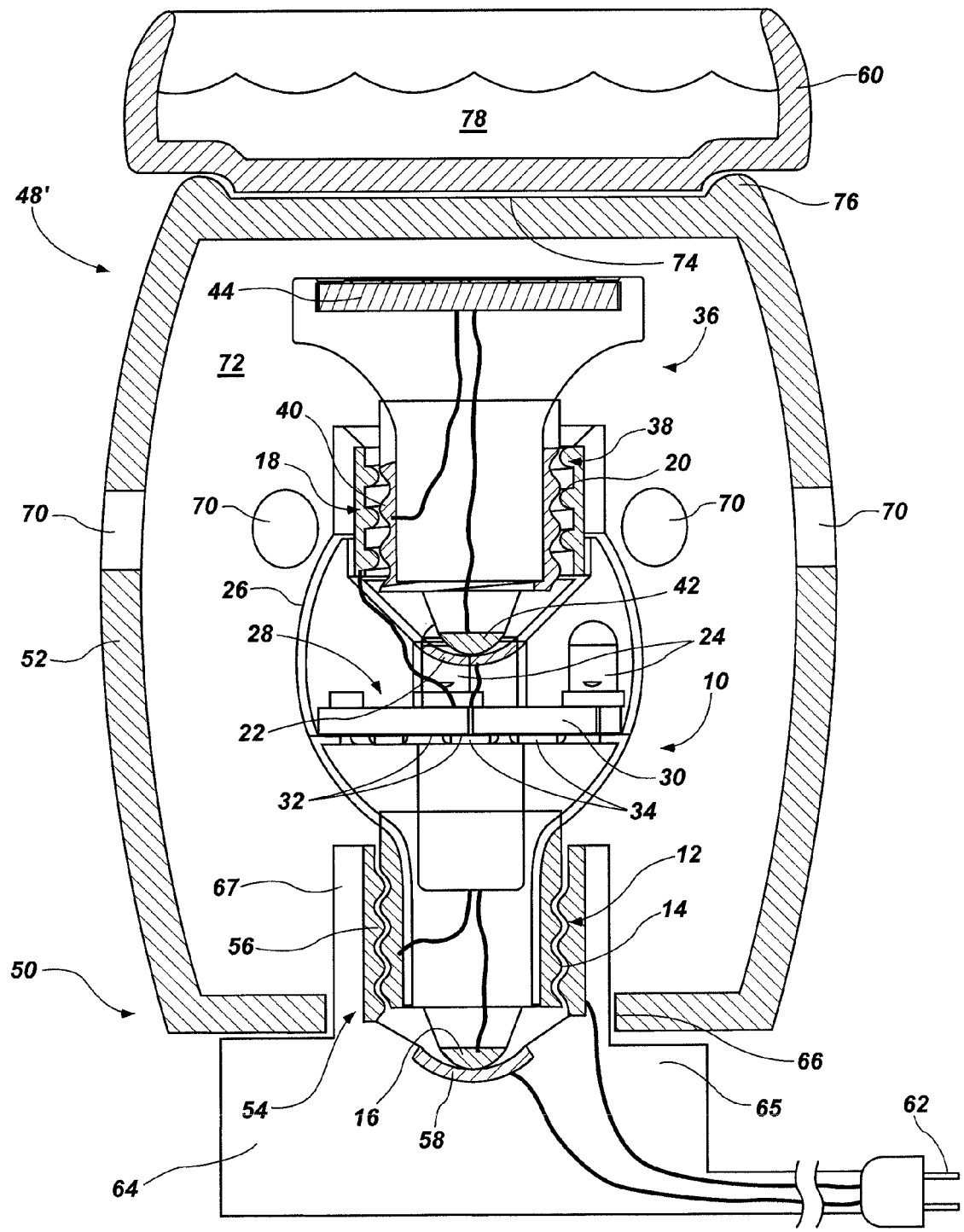
FIG. 11 illustrates simplified a cross-sectional view of another embodiment of a scent warmer.

Referring to FIG. 11, a simplified cross-sectional view of another embodiment of a scent warmer 48' is shown. The scent warmer 48' comprises a base structure 50 having an at least substantially hollow portion 52 defining a cavity configured to receive at least one lighting module 10 and at least one heating module 36 at least partially therein. The at least substantially hollow portion 52 may comprise at least one light hole 70 formed in a side surface 72 thereof. For example, the at least substantially hollow portion 52 may comprise a plurality of light holes 70 through which at least some light is allowed to pass. Thus, the at least substantially hollow portion 52 may be configured to permit light emitted by the lighting module 10 to pass from an interior of the at least substantially hollow portion 52 to an exterior of the at least substantially hollow portion 52.

The support member 64 of the base structure 50 may be configured to rest on a surface of another structure, rather than be supported by rigid connection to the electrical power source interface 62, in some embodiments. In such embodiments, the electrical power source interface may not be rigidly connected to the support member 64. For example, the electrical power source interface 62 may be physically connected to the support member 64 using a conventional, flexible power cord configuration.

The base structure 50 may include a receptacle 60 that is removable from the at least substantially hollow portion 52. For example, the at least substantially hollow portion 52 may include an upper surface 74 on which the receptacle 60 may be disposed during use and an upwardly projecting ridge 76 that may retain and align the receptacle 60 on the upper surface 74. By making the receptacle 60 a separate structure from the at least substantially hollow lower portion 52, the receptacle 60 may be easily removed to exchange for another receptacle 60 (e.g., to change the appearance of the scent warmer 48 or to replace a broken or defective receptacle 60) or to clean the receptacle 60, for example.

The base structure 50 may comprise an electrical power source interface 62, such as, for example, a standard electrical power plug, in electrical communication with the female threaded electrical connector 54 of the base structure 50. The electrical power source interface 62 may extend from a support member 64 of the base structure 50. The female threaded electrical connector 54 of the base structure 50 may be disposed in the support member 64. In addition, the at least substantially hollow portion 52 may be disposed over, and rest on, the support member 64. Thus, when assembling the scent warmer 48, a heating module 36 may be threadedly engaged with a lighting module 10, which may be threadedly engaged with the female threaded electrical connector 54 disposed in the support member 64. A hole 66 formed in the bottom of at least substantially hollow portion 52 may be positioned over and aligned with the assembly of the heating module 36, the lighting module 10, and the support member 64. The at least substantially hollow portion 52 may be lowered, and the assembly of the heating module 36, the lighting module 10, and the support member 64 may be at least partially positioned within the cavity defined by the at least substantially hollow portion 52. The at least substantially hollow portion 52 may rest on and be supported by the support member 64, for example on an annular shoulder 65 surrounding protrusion 67 surrounding female threaded electrical connector 54. The electrical power source interface 62 may be rigidly connected to the support member 64. Thus, the scent warmer 48 may be configured to be supported by an electrical power source, such as, for example, an electrical power socket.

The base structure 50 may optionally comprise a user control interface 68 (not shown in FIG. 11), as described above with respect to FIG. 10. The user control interface 68 may be configured to receive input from a user to alter the operation of the scent warmer 48. For example, the user control interface 68 may comprise a switch that may be used to open and close the electrical path from the electrical power source interface 62 to the female threaded electrical connector 54 of the base structure 50 and the other components in electrical communication therewith. Thus, the user control interface 68 may enable a user to turn the scent warmer 48 on and off. In addition, the user control interface 68 may be configured to change at least one of intensity of light emitted by the lighting module 10, color of light emitted by the lighting module 10, and flickering of light emitted by the lighting module 10 in response to a user input. In the embodiment of FIG. 11, for example, the user control interface may be incorporated in the flexible power cord.

During operation of a scent warmer 48 or 48', a scented material 78 may be disposed in the receptacle 60, and electrical power may be provided to the scent warmer 48 or 48', for example, by connecting the electrical power source interface 62 to an electrical power source or by providing an input to the user control interface 68 (see FIG. 9). The lighting module 10 may emit light, which may pass through to be visible at an exterior of the at least substantially hollow lower portion 52, and the heating module 36 may emit heat due to the electrical power provided thereto. Thus, the heating module 36 may heat the scented material 78 to cause the scented material to release a scent into the surrounding area. For example, the heating module 36 may heat the scented material 78 disposed in the receptacle 60 to a temperature of between about 40° C. and 70° C. As a continuing example, heating module 36 may heat the scented material 78 disposed in the receptacle 60 to a temperature of between about 50° C. and about 60° C.

By utilizing a modular lighting and heating approach, modules, such as the lighting and heating modules 10 and 36 described herein, a scent warmer 48 or 48' may be easily assembled by a user. In addition, a scent warmer 48 or 48' may be customized by the user, such as, for example, by omitting the lighting module 10 or by providing additional or different lighting modules 36 or other types of modules, where the various male and female threaded electrical connectors 12, 18, 38, and 54 are of compatible types and sizes. Of course, to provide desired proximity of a heating module 36 to receptacle 60 if a lighting module 10 is not employed, a spacer module (not shown) of a height corresponding to a lighting module and comprising a lower male threaded electrical connector and an upper female threaded electrical connector with conductive paths therebetween may be installed.

Moreover, the use of interchangeable lighting and heating modules 10 and 36 may enable simple repair of a scent warmer 48 or 48' where, for example, at least one of the lighting and heating modules 10 and 36 is broken, is defective, or has otherwise exceeded its useful life. For example, a user may easily remove at least one of the lighting module 10 and the heating module 36 from a scent warmer 48 or 48' by disengaging the male threaded electrical connector 12 or 38 from the respective female threaded electrical connector 18 or 54 with which it was threadedly engaged. The removed lighting or heating module 10 or 36 may then be replaced by another lighting or heating module 10 or 36 by engaging the male threaded electrical connector 12 or 38 with its respective female threaded electrical connector 18 or 54.

Furthermore, the use of interchangeable lighting and heating modules 10 and 35 may enable a user to retrofit an existing scent warmer by replacing the existing sources of light and/or heat. A user may retrofit a scent warmer by removing an existing source of light and/or heat. For example, a user may disengage a male threaded electrical connector (e.g., a standard E12 size Edison screw fitting, which may correspond to a standard candelabra size Edison screw fitting as used in North America) of an incandescent lamp, which was acting as a source of both heat and light, from a female threaded electrical connector of a scent warmer with which it was threadedly engaged. The user may then replace the source of light and/or heat with at least one of a lighting module and a heating module. For example, the user may threadedly engage a male threaded electrical connector 12 of a lighting module 10 of an assembly 46 of the lighting module 10 and a heating module 36 with the female threaded electrical connector of the scent warmer.

While embodiments of the foregoing disclosure have been described in the context of the use of threaded male and female electrical connections, these embodiments and the scope of the invention are not so limited. For example, other types of electrical connection may be employed, including without limitation bayonet-type electrical connections, keyed-type electrical connections, surface contacts, and other suitable connection types. Moreover, the relative disposition of male and female electrical connectors in the heating and lighting modules, as well as in the base structure, may be altered. For example, male electrical connectors may be used on both side of a lighting module, and a heating module provided with a female electrical connector.

While the present invention has been described herein with respect to certain embodiments, those of ordinary skill in the art will recognize and appreciate that it is not so limited. Rather, many additions, deletions, and modifications to the embodiments described herein may be made without departing from the scope of the invention as hereinafter claimed, including legal equivalents. In addition, features from one embodiment may be combined with features of another embodiment while still being encompassed within the scope of the invention as contemplated by the inventor.

Conclusion

In some embodiments, lighting modules for use with a scent warmer comprise at least one electrical light source. A first electrical connector is in electrical communication with and disposed on a first side of the at least one electrical light source. A second electrical connector is disposed on another side of the at least one electrical light source and in electrical communication with the first electrical connector.

In other embodiments, modular assemblies for use with a scent warmer comprise a lighting module and a heating module. The lighting module comprises at least one electrical light source. A first electrical connector is in electrical communication with and disposed on a first side of the at least one electrical light source. A second electrical connector is disposed on another side of the at least one electrical light source and in electrical communication with the first electrical connector. The heating module comprises a third electrical connector engaged and in electrical communication with the second electrical connector of the lighting module. A heating element is located at an end of the heating module opposing the third electrical connector and in electrical communication with the third electrical connector of the heating module.

In additional embodiments, scent warmers configured to heat a scented material and emit light comprise a base structure, a lighting module, and a heating module. The base structure comprises an at least substantially hollow portion defining a cavity configured to receive at least one lighting module and at least one heating module at least partially therein, a female electrical connector, and a receptacle disposed over the at least substantially hollow portion for supporting a scented material. The lighting module is at least partially disposed in the at least substantially hollow portion of the base structure and comprises at least one electrical light source. A male electrical connector is engaged and in electrical communication with the female electrical connector of the base structure and disposed on a first side of the at least one electrical light source. A female electrical connector is disposed on another side of the at least one electrical light source and in electrical communication with the male electrical connector. The heating module is at least partially disposed in the at least substantially hollow portion of the base structure and comprises a male electrical connector engaged and in electrical communication with the female electrical connector of the lighting module. A heating element is in electrical communication with the male electrical connector of the heating module.

In still other embodiments, methods of forming a lighting module for use with a scent warmer configured to heat a scented material and emit light comprise electrically connecting at least one electrical light source to a male electrical connector on a first side of the at least one electrical light source. A female electrical connector on another side of the at least one electrical light source is electrically connected to the male electrical connector.

In yet additional embodiments, methods of forming a scent warmer comprise forming a base structure, forming a lighting module, and forming a heating module. Forming a base structure comprises defining a cavity configured to receive at least one lighting module and at least one heating module in an at least substantially hollow lower portion. A receptacle is configured for supporting a scented material during use of the scent warmer to engage an upper portion of the at least substantially hollow lower portion. Forming a lighting module configured to be at least partially disposed in the at least substantially hollow base portion comprises electrically connecting at least one electrical light source to a male electrical connector configured to engage a female electrical connector of the base structure and disposed on a first side of the at least one electrical light source. A female electrical connector disposed on another side of the at least one electrical light source is electrically connected to the male electrical connector. Forming a heating module configured to be at least partially disposed in the at least substantially hollow base portion comprises electrically connecting a heating element to a male electrical connector configured to engage the female treaded electrical connector of the lighting module.

In further embodiments, methods of assembling a scent warmer configured to heat a scented material and emit light comprise engaging a male electrical connector of a lighting module with a female electrical connector of a base structure. A male electrical connector of a heating module is engaged with a female electrical connector of the lighting module disposed on a side of at least one electrical light source of the lighting module opposing another side on which the male electrical connector of the lighting module is disposed. A hollow portion of the base structure is disposed over the heating module and the lighting module to rest on a supporting portion of the base structure.

In still further embodiments methods of repairing a scent warmer comprise removing at least one of a lighting module and a heating module by disengaging a male electrical connector of the at least one of the lighting module and the heating module from a female electrical connector with which it was engaged. The at least one of the lighting module and the heating module is replaced by engaging a male electrical connector of at least one of another lighting module and another heating module with the female electrical connector.

In additional embodiments, methods of retrofitting a scent warmer comprise removing an incandescent lamp by disengaging a male threaded electrical connector of the incandescent lamp from a female electrical connector with which it was threadedly engaged. The incandescent lamp is replaced with at least one of a lighting module and a heating module by engaging a male threaded electrical connector of the at least one of a lighting module and a heating module with the female threaded electrical connector.

What is claimed is:

1. A method of assembling a scent warmer configured to heat a scented material and emit light, comprising:
   engaging a male electrical connector of a lighting module with a female electrical connector of a base structure;
   engaging a male electrical connector of a heating module with a female electrical connector of the lighting module, the female electrical connector of the lighting module being disposed on a side of at least one electrical light source of the lighting module opposing another side on which the male electrical connector of the lighting module is disposed; and
   disposing a hollow portion of the base structure over the heating module and the lighting module to rest on a supporting portion of the base structure.

2. The method of claim 1, further comprising disposing a removable receptacle over the hollow portion of the base structure, the receptacle being sized and shaped to support a scented material therein.

3. A method of repairing a scent warmer, comprising:
removing at least one of a lighting module comprising a male electrical connector on a first side of an electrical light source of the lighting module and a female electrical connector on a second, opposite side of the electrical light source of the lighting module, the male electrical connector of the lighting module being in electrical communication with the female electrical connector of the lighting module, and a heating module comprising a male electrical connector by disengaging the male electrical connector of the at least one of the lighting module and the heating module from a female electrical connector with which it was engaged; and
replacing the at least one of the lighting module and the heating module by engaging a male electrical connector of another lighting module with a female electrical connector of a base structure and engaging the male electrical connector of the heating module with the female electrical connector of the other lighting module or by engaging a male electrical connector of another heating module with the female electrical connector of the lighting module.

4. A method of retrofitting a scent warmer, comprising:
removing an incandescent lamp by disengaging a male electrical connector of the incandescent lamp from a female electrical connector of a base structure with which it was engaged; and
replacing the incandescent lamp with a lighting module comprising a male electrical connector on a first side of an electrical light source of the lighting module and a female electrical connector on a second opposite side of the electrical light source of the lighting module, the male electrical connector of the lighting module being in electrical communication with the female electrical connector of the lighting module, and a heating module comprising a male electrical connector by engaging the male electrical connector of the lighting module with the female electrical connector of the base structure and engaging the male electrical connector of the heating module with the female electrical connector of the lighting module.

5. The method of claim 1, wherein engaging the male electrical connector of the lighting module with the female electrical connector of the base structure comprises engaging the male electrical connector of the lighting module with the female electrical connector of the base structure, the at least one electrical light source of the lighting module being at least one of at least one light emitting diode (LED) and at least one compact fluorescent lamp (CFL).

6. The method of claim 1, wherein engaging the male electrical connector of the lighting module with the female electrical connector of the base structure, the at least one electrical light source of the lighting module being at least one of at least one light emitting diode (LED) and at least one compact fluorescent lamp (CFL), comprises engaging the male electrical connector of the lighting module with the female electrical connector of the base structure, the at least one electrical light source of the lighting module being a plurality of LEDS.

7. The method of claim 1, wherein engaging the male electrical connector of the lighting module with the female electrical connector of the base structure comprises electrically connecting circuitry of the lighting module to the female electrical connector of the base structure.

8. The method of claim 7, wherein electrically connecting the circuitry of the lighting module to the female electrical connector of the base structure comprises electrically connecting circuitry of the lighting module configured to control at least one of color, flickering, and intensity of light of the at least one electrical light source to the female electrical connector of the base structure.

9. The method of claim 1, wherein engaging the male electrical connector of the lighting module with the female electrical connector of the base structure and engaging the male electrical connector of the heating module with the female electrical connector of the lighting module comprise engaging a male Edison screw fitting of the lighting module with a female Edison screw fitting of the base structure and engaging a male Edison screw fitting of the heating module with a female Edison screw fitting of the lighting module.

10. The method of claim 1, wherein engaging the male electrical connector of the heating module with the female electrical connector of the lighting module comprises supporting a weight of the heating module on a translucent or transparent cover member of the lighting module, the cover member structurally connecting the female electrical connector of the lighting module to the male electrical connector of the lighting module, the at least one electrical light source being located within the cover member.

11. The method of claim 1, wherein engaging the male electrical connector of the heating module with the female electrical connector of the lighting module comprises engaging the male electrical connector of a heating module comprising a resistive heating element configured to heat to a temperature of between about 45° C. and about 70° C. with the female electrical connector of the lighting module.

12. The method of claim 1, wherein disposing the hollow portion of the base structure over the heating module and the lighting module to rest on the supporting portion of the base structure comprises disposing a hollow portion of the base structure comprising at least one translucent or transparent region over the heating module and the lighting module to rest on the supporting portion of the base structure.

13. The method of claim 1, further comprising positioning a scented material in a non-removable receptacle integral to the hollow portion.

14. The method of claim 2, further comprising positioning a scented material in the removable receptacle.

15. The method of claim 3, wherein engaging the male electrical connector of the other lighting module with the female electrical connector of the base structure comprises engaging the male electrical connector of the other lighting module with the female electrical connector of the base structure, the at least one electrical light source of the lighting module being at least one of at least one light emitting diode (LED) and at least one compact fluorescent lamp (CFL).

16. The method of claim 3, wherein replacing the at least one of the lighting module and the heating module by engaging the male electrical connector of the other lighting module with the female electrical connector of the base structure and engaging the male electrical connector of the heating module with the female electrical connector of the other lighting module or by engaging the male electrical connector of the other heating module with the female electrical connector of the lighting module comprises replacing the at least one of the lighting module and the heating module by engaging a male Edison screw fitting of the other lighting module with a female Edison screw fitting of the base structure and engaging a male Edison screw fitting of the heating module with a female Edison screw fitting of the lighting module or by engaging a male Edison screw fitting of the other heating module with a female Edison screw fitting of the lighting module.

17. The method of claim 3, wherein replacing the at least one of the lighting module and the heating module by engaging the male electrical connector of the heating module with the female electrical connector of the lighting module or by engaging a male electrical connector of another heating module with the female electrical connector of the lighting module comprises replacing the at least one of the lighting module and the heating module by engaging the male electrical connector of the heating module with the female electrical connector of the other lighting module, the heating module comprising a resistive heating element configured to heat to a temperature of between about 45° C. and about 70° C., or by engaging a male electrical connector of another heating module with the female electrical connector of the lighting module, the other heating module comprising a resistive heating element configured to heat to a temperature of between about 45° C. and about 70° C.

18. The method of claim 4, wherein engaging the male electrical connector of the lighting module with the female electrical connector of the base structure comprises engaging the male electrical connector of the lighting module with the female electrical connector of the base structure, the at least one electrical light source of the lighting module being at least one of at least one light emitting diode (LED) and at least one compact fluorescent lamp (CFL).

19. The method of claim 4, wherein engaging the male electrical connector of the lighting module with the female electrical connector of the base structure and engaging the male electrical connector of the heating module with the female electrical connector of the lighting module comprise engaging a male Edison screw fitting of the lighting module with a female Edison screw fitting of the base structure and engaging a male Edison screw fitting of the heating module with a female Edison screw fitting of the lighting module.

20. The method of claim 4, wherein engaging the male electrical connector of the heating module with the female electrical connector of the lighting module comprises engaging the male electrical connector of a heating module comprising a resistive heating element configured to heat to a temperature of between about 45° C. and about 70° C. with the female electrical connector of the lighting module.

* * * * *